United States Patent [19]

Vaillancourt

[11] Patent Number: 5,429,610
[45] Date of Patent: Jul. 4, 1995

[54] DUAL CHAMBER SYRINGE FOR COLLECTING SAMPLES AND BLOOD COLLECTING SYSTEM

[76] Inventor: Vincent L. Vaillancourt, 14 Bunyan Dr., Livingston, N.J. 07039

[21] Appl. No.: 154,874

[22] Filed: Nov. 19, 1993

[51] Int. Cl.$^6$ ............................................. A61M 5/00
[52] U.S. Cl. ............................ 604/191; 604/89; 604/210; 128/762; 128/760
[58] Field of Search ............... 128/760, 762, 763, 765, 128/766; 604/187, 191, 208, 210, 89, 90, 91

[56] References Cited

U.S. PATENT DOCUMENTS

| | | | |
|---|---|---|---|
| 2,875,761 | 3/1959 | Helmer et al. | 604/210 |
| 3,831,602 | 8/1974 | Broadwin | 604/210 |
| 3,938,505 | 2/1976 | Jamshidi | 304/210 X |
| 4,064,879 | 12/1977 | Leibinsohn | 604/210 X |
| 4,715,854 | 12/1987 | Vaillancourt | 604/208 X |
| 4,978,339 | 12/1990 | Labouze et al. | 604/210 X |

FOREIGN PATENT DOCUMENTS

| | | | |
|---|---|---|---|
| 351497 | 7/1905 | France | 604/210 |
| 9005555 | 5/1990 | WIPO | 128/765 |

*Primary Examiner*—Sam Rimell
*Attorney, Agent, or Firm*—Francis C. Hand

[57] ABSTRACT

The dual chamber syringe is employed for collecting blood samples. The syringe includes a plunger which is connected to a first piston which, in turn, is connected via a string to a second piston. A passageway is formed in the wall of the syringe barrel to communicate the duct at the forward end of the barrel with the chamber between the two pistons. Thus, upon withdrawal of the plunger from a barrel, fluid flows into the chamber created between the two pistons. Subsequent movement of the two pistons in unison causes a whole blood sample to be drawn into the foremost chamber within the barrel. The syringe can be subsequently connected with a vacutainer via a needle assembly so as to discharge the whole blood sample into the vacutainer for subsequent testing procedures. The discard fluid can be separately dispensed into another container. A catch is employed on the syringe barrel or on the plunger to positively prevent a movement of the plunger into the barrel which would cause a discharge of the discard fluid.

15 Claims, 1 Drawing Sheet

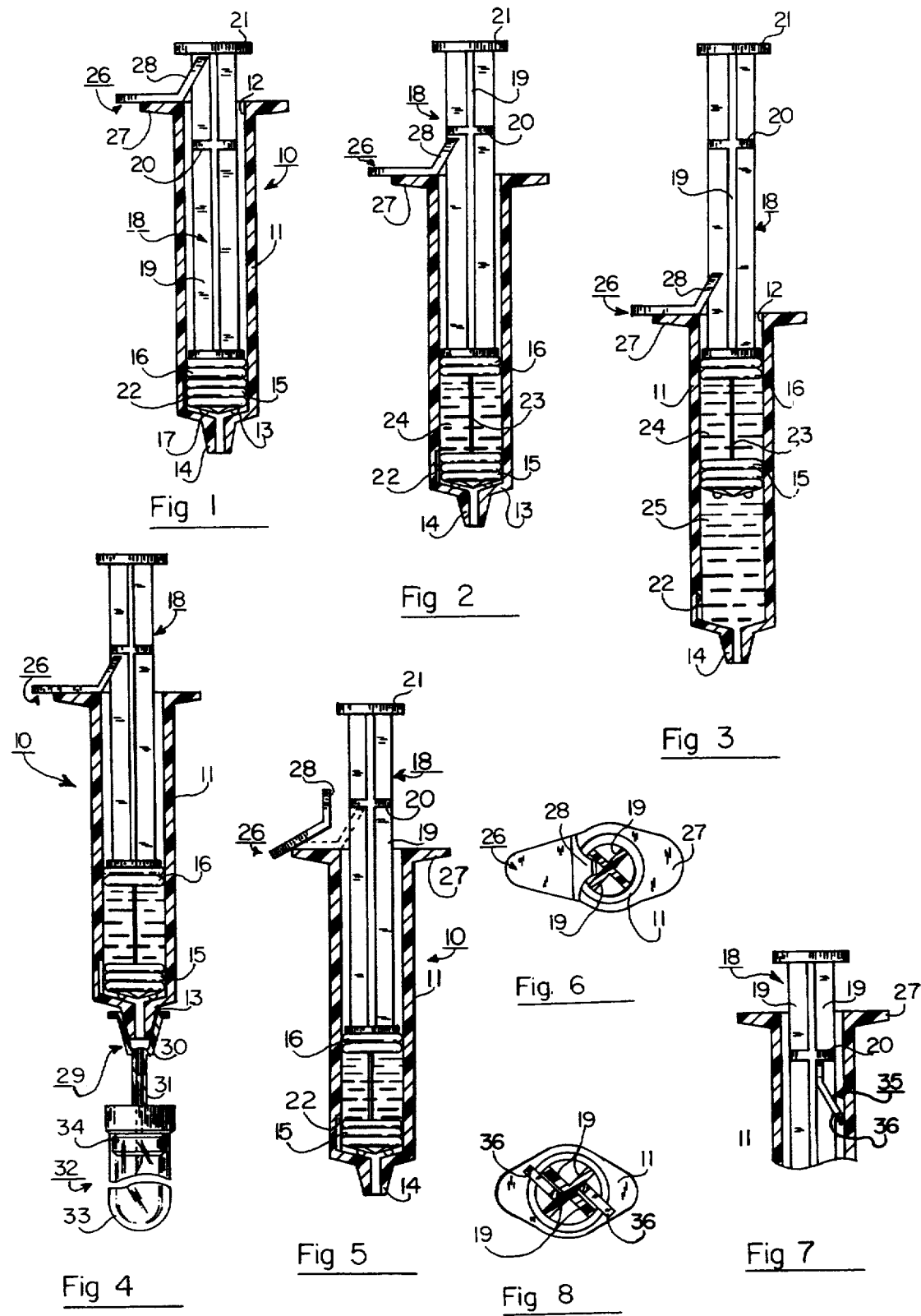

DUAL CHAMBER SYRINGE FOR COLLECTING SAMPLES AND BLOOD COLLECTING SYSTEM

This invention relates to a dual chamber syringe for collecting blood samples and to a blood collecting system.

As is known, various types of techniques have been employed for the collection of blood from a patient. Generally, hospitals and homecare companies are now required to insure that precautions against occupational exposure to blood and other potentially infectious materials are followed by all employees in the healthcare setting, from the laboratory to the housekeeping department. Many of the precautions are based upon a belief that compliance with universal precautions will provide safeguards against transmission of various viruses and organisms such as HIV.

One of the areas of concern in a healthcare setting is the possibility of a needlestick. This is because needlesticks are believed to present the greatest danger to nurses and lab personnel because of the variety of procedures involved in the drawing of blood from a patient. Thus, nurse safety is at risk each time a needle is used to sample or transfer blood, for example, to an evacuated tube. There is also a potential for exposure to dangerous pathogens each time when blood is extracted from a catheter. Patient safety is also threatened by the risk of catheter contamination and the potential for nosocomial infections.

Still further, other concerns arise when taking blood samples from a patient. For example, excessive sampling may result in an excessive blood loss which may threaten a patient's safety and which may necessitate a transfusion. Also, inconsistent discard volumes may yield inaccurate lab values resulting in a possible misdiagnosis and mistreatment.

In the past, when drawing sodium heparinized blood from a patient use has usually been made of two syringes for a blood draw from a central venous catheter. However, this requires not only the added costs of materials but also additional time on the part of the nurse or person drawing blood.

As is known, blood sampling usually involves the collection of whole blood which contains all the blood elements. That is, whole blood is the sample of choice for blood gas analysis, determination of hemoglobin derivatives and the measurement of RBC constituents. In addition, most routine hematologic studies, such as complete blood count, erythrocyte sedimentation rate, reticulocyte and platelet counts as well as osmotic fregility tests require whole blood samples.

Plasma is the liquid part of whole blood which contains all the blood proteins; serum is the liquid that remains after whole blood clots. Plasma and serum samples which contain most of the physiologically and clinically significant substances found in blood are used for most biochemical immunologic and coagulation studies. They also provide useful electrolyte evaluation, enzyme analysis, glucose concentration, protein determination and bilirubin level.

Sample quantities required for diagnostic studies depend on the laboratory, available equipment and the type of test. The desired sample quantity determines the collection procedure and the type and size of container. For example, a single venipuncture with a conventional glass or disposable syringe can provide 15 millileters of blood. This is usually sufficient for many hematologic, immunologic, chemical and coagulation tests but hardly enough for a series of tests.

In order to avoid multiple venipunctures when tests require a large blood sample, use has been made of an evacuated tube system, that is, a vacutainer with interchangeable glass tubes, optional draw capacities and a selection of additives. Evacuated tubes are commercially prepared with and without additives (usually indicated by a color-coated stopper) and with enough vacuum to draw a predetermined blood volumne, for example, from two to twenty milliliters per tube. The nature of the tests and patient's age and condition usually determine the appropriate blood sample, collection site and technique. Most tests require a venous sample. Although a relatively simple procedure, venipuncture must be performed carefully to avoid egmolysis or hemoconcentration of the sample to prevent hemotoma formation and to prevent damage to the patient's veins.

In order to avoid discomfort from repeated infusion of drug products and blood collection stickings, central venus access devices have been utilized with critical care and longterm care patients. These devices may be simple or multiple lumen devices, Groshongs, PICC lines, implantable ports and arterial blood pressure lines.

Currently, blood draws from the known vascular access devices are performed by two primary methods.

In one case, use has been made of two plastic disposable syringes. One syringe is used to draw up discard which is mixed with saline or heparinized saline flush solution. The volume of this discard solution is usually five or ten millileters. However, this blood is not suitable for testing and would give false results. The second syringe is then used to draw up the pure blood sample for the prescribed test procedure. The volume of the pure blood sample is dependent on the test or tests needed to be performed but usually used in the range of from two to twenty milliliters. The pure blood is then transfered to the appropriate evacuated container or containers, i.e. a vacutainer, for the actual test and is then transported to the laboratory.

The second method of blood draw collects the sample by using a standard blood collection syringe and needle affixed to the vascular access device while employing the appropriate evacuated container for the desired test procedure. This method is not recommended by many catheter manufacturers because of the potential for collapsing the catheter with the vacuum in the collection tube. In particular, the method is not usually recommended for PICC lines, Groshong catheters and Landmark catheters.

The practice of home intravenous therapy has become increasingly popular with patients receiving intravenous antibiotics, chemotherapy, hydration fluids and total parenteral nutrition at home. Usually, the patients benefit in many ways from such therapy, the most obvious benefit being financial since costs are generally less than in institutional intravenous therapy.

A variety of venous access devices have been developed for intravenous therapy and may include single, dual or triple lumens and may be external, peripheral or central or implanted. In many cases, a discard of blood is made followed by collection of a whole blood sample. Thereafter, flushing is usually performed with heparin or a saline solution.

Accordingly, it is an object of the invention to reduce the risk of inadvertant blood spills or leakages when drawing blood from a patient.

It is another object of the invention to utilize one syringe for obtaining a whole blood sample from a patient.

It is another object of the invention to reduce the time and materials required for obtaining a whole blood sample from a patient.

It is another object of the invention to collect a blood sample and maintain the sample in a contamination-free manner.

It is another object of the invention to separately obtain a discard and a whole blood sample from a patient in a sequential manner without contamination of the blood sample.

Briefly, the invention provides a dual chamber syringe for collecting blood samples. In addition, the invention provides a blood collecting system employing the dual chamber syringe with a storage device.

More particularly, the dual chamber syringe is comprised of a one-piece cylindrical barrel having an open end and a tip defining a closed end with a duct extending therefrom. In addition, the syringe employs a first or foremost piston which is slidably mounted in the barrel to move from a first position abutting the closed end to a second position spaced therefrom to define a first chamber for receiving a whole blood sample. A second or rearmost piston is also slidably mounted in the barrel to move between a first position adjacent the first piston and a second position spaced therefrom to define a second chamber therebetween for receiving a discard. A plunger is also connected to the second piston to extend from the barrel. This plunger serves to effect movement of the second piston relative to the barrel.

The syringe also has a passageway disposed between the foremost piston and the barrel to define a communicating path between the duct in the tip of the barrel and a point between the two pistons. Still further, a collapsible means connects the two pistons so as to move the foremost piston with the rearmost piston after a predetermined movement of the rearmost piston has caused a filling of the second chamber with a first flow of blood from a patient so as to allow filling of the first chamber of the barrel with a second flow of blood from the patient.

Basically, the dual chamber syringe is of a construction as described in U.S. Pat. No. 4,715,854.

In use, the dual chamber syringe may be connected to a venous access device through a needle asembly or directly so as to withdraw blood from a patient as the plunger is retracted relative to the barrel. In this respect, initial retraction of the plunger causes a first flow of blood along with fluids in the venous access device to flow about the first piston in the barrel into the chamber forming between the two pistons. Thereafter, upon continued retraction of the plunger and movement of the foremost piston via the collapsible means, blood is drawn into the foremost chamber then forming between the foremost piston and the closed end of the barrel. In this manner, a mixed whole blood sample, for example, including blood and other fluids from the access device, is collected in the rearmost or discard chamber while whole unadulterated blood is collected in the foremost chamber. The syringe can then be connected to a storage device so that the blood from the foremost chamber of the syringe can be discharged into the storage device upon movement of the plunger into the barrel.

The dual chamber syringe is also provided with a stop means for preventing movement of the plunger into the barrel after dispensing of the blood collected in the foremost chamber. This stop means prevents the discard in the rearmost chamber from inadvertantly being mixed with the pure blood. In those cases where the user wishes to expel the discard fluid, the stop means may be deactivated thereby freeing the plunger so as to be moved further into the barrel thereby discharging the discard from the rearmost chamber via the duct at the end of the syringe.

The stop means for preventing movement of the plunger completely into the barrel may be mounted on the barrel or on the plunger. In this respect, the stop means may be in the form of a catch mounted on the barrel for abutting the plunger in a given position thereof in order to prevent further movement of the plunger into the barrel. The catch may also be pivotally mounted on the barrel to pivot out of abutment with the plunger in order to permit movement of the plunger into the barrel to effect dispensing of the discard in the rearmost chamber.

The blood collecting system employs the dual chamber syringe as described above with a suitable storage device, for example, the storage device may be in the form of a vacuum tube system, that is, a vacutainer.

These and other objects and advantages of the invention will become more apparent from the following detailed description taken in conjunction with the accompanying drawings wherein:

FIG. 1 illustrates a part cross-sectional view of a dual chamber syringe constructed in accordance with the invention;

FIG. 2 illustrates a position of the syringe of FIG. 1 during withdrawal of a discard from a patient;

FIG. 3 illustrates a view of the syringe of FIG. 1 during withdrawal of a whole blood sample from a patient in accordance with the invention;

FIG. 4 illustrates the syringe of FIG. 1 during dispensing of a whole blood sample into a vacutainer;

FIG. 5 illustrates a position of the syringe of FIG. 1 for dispensing of the discard which has been collected;

FIG. 6 illustrates a plan view of the stop means of FIG. 1 for preventing movement of the plunger into the syringe in accordance with the invention;

FIG. 7 illustrates a partial cross-sectional view of a modified stop means in accordance with the invention; and FIG. 8 illustrates a plan view of the stop means of FIG. 7 in an active position in accordance with the invention.

Referring to FIG. 1, the dual chamber syringe 10 is constructed in a manner similar to that as described in U.S. Pat. No. 4,715,854 and is used for collecting blood samples. To this end, the syringe 10 includes a one-piece cylindrical barrel 11 having an open end 12 and a tip 13 defining a closed end with a duct 14 extending therefrom. The barrel 11 may be made of any conventional materials suitable for syringes and may be provided with a suitable scale or marking indicative of the volume. As indicated, the tip 13 is of connical shape while the duct 14 is centrally located on the axis of the barrel 11.

In addition, the syringe 10 includes a pair of pistons 15, 16, each of which is slidably mounted in the barrel 11. The foremost piston 15 is movable from a first position abutting the closed end of the barrel 11 to a second position spaced therefrom to define a first chamber therebetween (see FIG. 3). In addition, the foremost piston 15 has a plurality of protuberances 17, for example, in the form of beads at the forward end so as to provide a slight spacing or gap between the foremost piston 15 and the tip 13 of the barrel 11. The second or rearmost piston 16 is movable between a position as shown in FIG. 1 adjacent the foremost piston 15 and a second position spaced therefrom to define a second chamber as indicated in FIG. 2.

The syringe 10 includes a plunger 18 which is connected to the rearmost piston 16 and which extends from the barrel 11. This plunger 18 is of conventional structure and is used to move the pistons 15, 16 relative to the barrel. As indicated, the plunger 18 has four ribs 19 defining a cruciform shape, a cross-piece 20 at an intermediate point and a finger-gripping plate 21 at the end.

A passageway 22 is disposed between the foremost piston 15 and the barrel 11 to define a communicating path between the duct 14 and a point between the pistons 15, 16 with the foremost piston in the first position thereof as indicated in FIG. 1. In addition, baffles (not shown) may be provided within the passageway in a manner as described in U.S. Pat. No. 4,715,854.

A collapsible means in the form of a string 23 (see FIG. 2) is secured to and between the pistons 15, 16. This string 23 serves to connect the pistons 15, 16 while causing the foremost piston 15 to move with the rearmost piston 16 after a predetermined movement of the rearmost piston 16 from the position indicated in FIG. 1 to the position indicated in FIG. 2. During this time, a chamber 24 between the two pistons 15, 16 can be filled with a first flow of blood from a patient.

As indicated in FIG. 3, continued movement of the plunger 18 out of the barrel 11 causes the two pistons 15, 16 to move rearwardly thereby drawing blood into a second chamber 25 between the foremost piston 15 and the closed end of the barrel 11.

A stop means 26 is mounted on a finger-gripping end 27 of the barrel 11 for preventing movement of the plunger 18 into the barrel 11 after dispensing of blood collected in the foremost chamber 25 so as to prevent dispensing of the fluid in the rearmost chamber 24 as indicated in FIG. 4.

The stop means 26 includes a pivotally mounted catch 28 which is able to pivot out of abutment with the plunger 18 to permit movement of the plunger 18 out of the barrel 11, for example, from the position shown in FIG. 1 to the position shown in FIG. 3. In this respect, the catch 28 is in the form of a tab which is pushed aside by the cross-piece 20 on the plunger 18 during an upward movement of the plunger 18 as viewed. However, the catch 28 snaps back into the position as indicated in FIG. 2 so as to abut the cross-piece 20 and thereby prevent a return movement of the plunger 18 into the barrel 11. The catch 28 may also be pivoted away from the plunger 18 as indicated in FIG. 5 under a manually applied force so as to permit the plunger 18 to move into the barrel 11 to effect dispensing of blood from the rearmost chamber 24.

The entire catch 28 may be pivotally mounted on the end of the barrel 11 so as to pivot between a position in abutment with the cross-piece 20 of the plunger 18 and a position spaced from the plunger 18. Referring to FIG. 6, the forward portion of the safety catch 28 may be of narrowed shape to fit between the ribs 19 of the plunger 18.

The safety catch 28 which is used may be attached to the finger grip 27 of the syringe 10 using adhesive, by being staked in place or by being molded with the syringe finger grip 27. In addition, the safety catch 28 may be provided with a breakaway tab (not shown) which can be manually broken off when a discard fluid is to be discharged from the syringe.

Refering to FIG. 4, the syringe 10 is fitted with a needle assembly 29 for penetrating an injection port, e.g. a rubber septum or a Y-Site on an administration set. However, there are some cases, such as an opening in a central line at a luer connection, in which the syringe 10 can be directly inserted in the line so that a needle is not required.

As shown, the needle assembly 29 includes a hub 30 for mounting onto the tip 13 of the syringe barrel 11 and a hollow needle 31 secured to and extending from the hub 30. The mounting of the hub 30 to the tip 13 of the barrel may be of any suitable type, for example a luer lock, a luer slip or a threaded connection (not shown) may be used to connect the hub 30 to the barrel tip 13.

In use, the syringe 10 is employed with a storage device 32 for collecting a blood sample. Such a storage device 32 may be in the form of a vacuum tube, such as vacutainer, which is of known construction, for example, having an evacuvated glass tube 33 with a rubber stopper or septum 34 at the open end.

In order to obtain a blood sample or other fluid sample, from a patient, the needle 31 of the needle assembly 29 mounted on the syringe barrel 11 is passed in known fashion into a venous access device (not shown) implanted in a patient, Next, the plunger 18 is retracted relative to the barrel 11 thereby causing a first flow of whole blood as well as fluid in the access device to be drawn into the rearmost chamber 24 located between the pistons 15, 16 (see FIG. 2). During this time, the initial blood flow flows through the duct 14 and passageway 22 into the rearmost chamber 24. At the same time, the cross-piece 20 of the plunger 18 moves past the catch 28 of the stop means 26. Typically, about 5 cc of fluid would be drawn from the access device. Continued movement of the plunger 18 out of the barrel 11 causes the string 23 to pull the foremost piston 15 along with the plunger 18 and rearmost piston 16. This, in turn, causes a sample of whole blood to flow from the access device through the needle 31 and the duct 14 directly into the chamber 25 between the piston 15 and the closed end of the barrel 11. Since both pistons 15, 16 are in frictional contact with the barrel 11, the rearmost chamber which contains the first blood flow (i.e. the discard) is sealed off not only from the outside environment but also from the foremost chamber 25 which now contains a whole blood sample.

In cases where the syringe 10 is not provided with a needle, the tip 13 of the syringe 10 can be directly connected to a luer connection in order to obtain a fluid sample from a patient. In such cases, in order to discharge the fluid sample into a vacutainer 32, a needle assembly 29 would be secured to the tip 13 of the syringe barrel 11 in order to effect discharge through the rubber septum 34 on the vacutainer 32.

After an appropriate blood sample has been withdrawn from the patient, for example, as indicated in FIG. 3, the syringe 10 is removed from the patient and connected to the vacutainer 32 as indicated in FIG. 4. In this respect, the needle 38 pierces through the rubber septum 33 of the vacutainer 32 so that the whole blood sample in the foremost chamber 25 can be dispensed into the vacutainer 32.

Referring to FIG. 4, when the plunger 18 is pushed into the barrel 11 from the position shown in FIG. 3, the blood in the foremost chamber 25 is forced out of the duct 14 while the discard fluid in the rearmost chamber 24 between the pistons 15, 16, being substantially incompressible, maintains the integrity of the chamber 24 so that the pistons 15, 16 move in unison.

As the foremost piston 15 approaches the closed end of the barrel 11, the piston 15 begins to move across the passageway 22. However, before the point is reached where the foremost piston 15 would permit communication of the passageway 22 with the rearmost chamber 24 between the pistons 15, 16, the safety catch 28 would abut the cross-piece 20 of the plunger 18 thus preventing further movement of the plunger 18. The syringe 10 would then be removed from the vacutainer 29. Thus, while a small amount of blood might remain within the duct 14 and passageway 22, this would prevent any discard fluid from flowing into the vacutainer 29 from the discard chamber 24.

The syringe 11 may then be provided with a cap or other sealing type of device (not shown) over the duct 14 to prevent dispensing of any further blood or discard. Where desired, the cap (not shown) can be removed so that the discard fluid can be dispensed from the syringe 10 into a suitable receptable (not shown), for example, for disposable purposes.

The point at which the foremost piston 15 ceases to move towards the tip 13 of the barrel 11 coincides with the position at which the catch 28 abuts the cross-piece 22 of the plunger 18. Thus, in those cases where the user wishes to expel the discard fluid, the safety catch 27 is pushed aside so that the plunger 18 can move further into the barrel 11.

Referring to FIG. 7 and 8, wherein like reference characters indicate like parts as above, a stop means 35 may be mounted on the plunger 18 for abutting against the syringe barrel 11. For example, the stop means 35 may include a pair of tabs 36 which are integral with the ribs 19 of the plunger 18 and which normally project beyond the plane of the syringe barrel 11. In addition, the tabs 33 are sufficiently resilient so as to be depressed inwardly of the plane of the barrel 11 so as to slide within the interior of the barrel 11 as indicated in FIG. 7. When the plunger 18 is moved in a direction out of the barrel 11, the tabs 36 are able to spring outwardly so that a return motion of the plunger 18 into the barrel 11 can be prevented when the tabs 33 engage against the end of the barrel 11.

Since the syringe 10 is capable of drawing two sequential samples from a venous access device, the time and material involved in drawing two samples from a patient can be reduced with respect to the previous use of two syringes for the same purpose.

The invention thus provides a dual chamber syringe which requires opening of a venous access system only once in order to obtain a whole blood sample from a patient for testing purposes. Accordingly, there is less exposure to blood and the liklihood of fewer spills.

Further, the dual chamber syringe allows a whole blood sample to remain contamination-free from the discard fluid which is initially drawn from the patient. In addition, the discard fluid will not mix with the whole blood sample when moving from the syringe to a vacutainer.

What is claimed is:

1. A dual chamber syringe for collecting fluid samples comprising
   a one piece cylindrical barrel having an open end and a tip defining a closed end with a duct extending therefrom;
   a first piston slidably mounted in said barrel to move from a first position abutting said closed end to a second position spaced therefrom to define a first chamber therebetween;
   a second piston slidably mounted in said barrel to move between a first position adjacent said first piston and a second position spaced therefrom to define a second chamber therebetween;
   a plunger connected to said second piston and extending from said barrel;
   a passageway disposed between said first piston and said barrel defining a communicating path between said duct and a point between said pistons with said first piston in said first position thereof;
   collapsible means connecting said pistons to move said first piston with said second piston after a predetermined movement of said second piston from said first piston and after filling of said second chamber with a first flow of fluid from a patient to allow filling of said first chamber with a second flow of fluid from the patient; and
   stop means for preventing movement of said plunger into said barrel after dispensing of the fluid collected in said first chamber and before dispensing of the fluid in the second chamber.

2. A dual chamber syringe as set forth in claim 1 wherein said stop means includes a catch fixedly mounted on said barrel for butting said plunger in a given position thereof to prevent movement of said plunger into said barrel.

3. A dual chamber syringe as set forth in claim 2 wherein said catch is pivotally mounted on said barrel to pivot out of abutment with said plunger to permit movement of said plunger into said barrel to effect dispensing of the blood in said first chamber through said duct.

4. A dual chamber syringe as set forth in claim 1 wherein said stop means is fixedly mounted on said plunger to abut said barrel to prevent movement of said plunger into said barrel.

5. A dual chamber syringe as set forth in claim 1 which further comprises a needle assembly mounted on said tip of said barrel, said needle assembly including a hollow needle in communication with said duct.

6. A dual chamber syringe for collecting blood samples comprising
   a cylindrical barrel having an open end and a closed end;
   a first piston slidably mounted in said barrel to move from a first position abutting said closed end to a first second position spaced therefrom to define a first chamber therebetween;
   a second piston slidably mounted in said barrel to move between a first position adjacent said first piston and a second position spaced therefrom to define a second chamber therebetween;
   a plunger connected to said second piston and extending from said barrel;
   a passageway disposed between said first piston and said barrel defining a communicating path between said duct and a point between said pistons with said first piston in said first position thereof;
   means connecting said pistons to move said first piston with said second piston after a predetermined movement of said second piston from said first piston and after filling of said second chamber with a first flow of blood from a patient to allow filling of said first chamber with a second flow of blood from the patient; and stop means for preventing movement of said plunger into said barrel after dispensing of the blood collected in said first chamber and before dispensing of the fluid in the second chamber.

7. A dual chamber syringe as set forth in claim 6 wherein said stop means includes a catch fixedly mounted on said barrel for butting said plunger in a given position thereof to prevent movement of said plunger into said barrel.

8. A dual chamber syringe as set forth in claim 6 which further comprises a needle assembly mounted on said tip of said barrel, said needle assembly including a hollow needle in communication with said duct.

9. A blood collecting system comprising a dual chamber syringe having a barrel with a duct at one end, a hollow needle extending from said barrel, a first piston in said barrel to define a first chamber with said one end of said barrel, a second piston in said barrel to define a second chamber between said pistons, a plunger connected to said second piston and extending from said barrel, a passageway disposed between said first piston and said barrel defining a communicating path between said duct and a point between said pistons with said first piston in said first position thereof, and collapsible means connecting said pistons to move said first piston with said second piston after filling of said second chamber with a first flow of blood from a patient to allow filling of said first chamber with a second flow of blood from the patient; stop means for preventing movement of the plunger into the barrel after dispensing the fluid collected in the first chamber, and before dispensing fluid collected in the second chamber;

a storage device for receiving said needle of said syringe to receive the blood from said first chamber upon movement of said plunger into said barrel.

10. A blood collecting system as set forth in claim 9 wherein said storage device is a vacuum tube having a seal at one end for sealing about said needle.

11. A blood collecting system as set forth in claim 9 wherein said syringe further includes a stop means for preventing movement of said plunger into said barrel after dispensing of the blood collected in said first chamber into said storage device.

12. A blood collecting system as set forth in claim 11 wherein said stop means is movable into a position to allow movement of said plunger into said barrel to effect dispensing of the blood collected in said second chamber through duct.

13. A method of collecting a blood sample from a venous access device implanted in a patient, said method comprising the steps of communicating a syringe barrel with the venous access device to receive a flow of fluid therefrom;

withdrawing a plunger having a first piston thereon in the syringe barrel to draw a mixture of fluid and whole blood from the access device into the syringe barrel into a first chamber between the first piston and a second piston disposed in the barrel; and continuing to withdraw the plunger to effect movement of both said pistons while drawing a flow of whole blood from the access device into the syringe barrel into a second chamber between the second piston and the syringe barrel.

14. A method as set forth in claim 13 which further comprises the steps of communicating the syringe barrel with a storage device for receiving blood from the syringe barrel; and thereafter moving the plunger into the barrel to move said second piston in a direction to expel the whole blood in said second chamber into the storage device.

15. A method as set forth in claim 14 which further comprises the step of automatically blocking movement of the piston into the syringe barrel to prevent expelling of the liquid from said first chamber.

* * * * *